United States Patent

Szantay et al.

[11] Patent Number: 6,093,720
[45] Date of Patent: Jul. 25, 2000

[54] TRANS APOVINCAMINIC ACID ESTER DERIVATIVES

[75] Inventors: Csaba Szantay; Istvan Moldvai; Andras Vedres; Maria Incze; Janos Kreidl; Laszlo Czibula; Maria Farkas Née Kiriak; Ida Deutsch Née Juhasz; Aniko Gere; Margit Pellionisz Née Paroczai; Erzsebet Lapis, all of Budapest; Andras Szekeres, Szolnok; Maria Zajer Née Balazs, Budapest; Adam Sarkadi, Diosd; Ferenc Auth, Budapest; Bela Kiss, Budapest; Egon Karpati, Budapest; Sandor Farkas, Budapest, all of Hungary

[73] Assignee: Richter Gedeon Vegyeszeti GmbH, Budapest, Hungary

[21] Appl. No.: 09/091,260

[22] PCT Filed: Dec. 13, 1996

[86] PCT No.: PCT/HU96/00075

§ 371 Date: Jun. 9, 1998

§ 102(e) Date: Jun. 9, 1998

[87] PCT Pub. No.: WO97/23481

PCT Pub. Date: Jul. 3, 1997

[30] Foreign Application Priority Data

Dec. 22, 1995 [HU] Hungary .................. 9503736

[51] Int. Cl.⁷ .................. A61K 31/435; C07D 471/22
[52] U.S. Cl. .................. 514/283; 546/51; 544/233.2; 544/269
[58] Field of Search .................. 514/283, 233.2, 514/269; 546/51; 544/111, 298

[56] References Cited

U.S. PATENT DOCUMENTS 4,486,437 12/1984 De Vincentiis ............ 424/256
4,614,824 9/1986 Kreidl et al. .............. 546/51

FOREIGN PATENT DOCUMENTS 1 258 071   8/1989   Canada .
25 31 108   2/1977   Germany .
60248688   12/1985   Japan .................. 514/283
2 124 214A  2/1984   United Kingdom .

OTHER PUBLICATIONS

Fitos, I. et al.: Binding of vinca alkaloid analogues to human serum albumin and to alpha–1–acid glycoprotein. Biochem. Pharm. vol. 41, pp. 377–383, 1991.

*Primary Examiner*—John Kight
*Assistant Examiner*—Charanjit S. Aulakh
*Attorney, Agent, or Firm*—Herbert Dubno; Jonathan Myers

[57] ABSTRACT

The invention relates to novel racemic and optically active trans apovincaminic acid ester derivatives of formula (I), $$R-O-(CH_2)_n-O-C(=O)- \quad (I)$$

$$Z-C=O \quad (a)$$

wherein R means hydrogen or a group (a), wherein Z stands for $C_{1-4}$ alkyl, optionally substituted aryl, aralkyl, heteroaryl or 14-eburnameninyl group; and n is an integer of 2, 3 or 4, as well as therapeutically acceptable salts thereof. The invention further relates to pharmaceutical compositions containing these compounds as well as a process for the preparation of the above compounds and compositions, and in addition, to a method of treatment. The novel compounds of Formula (I) exhibit particularly antioxidant, antiischemic as well as antiamnesic effects and are useful for inhibiting lipid peroxidation and for protection from or treatment of ischemia and amnesia as well as for treating various degenerative neurological diseases, e.g. Alzheimer's disease.

11 Claims, No Drawings

TRANS APOVINCAMINIC ACID ESTER DERIVATIVES

CROSS REFERENCE TO RELATED APPLICATIONS

This application is the U.S. National Phase of PCT/HU 96/00075 filed Dec. 13, 1996 now WO 87/23481, published Jul. 3, 1997 and claims under the International Convention the benefit of the priority of the Hungarian Patent Application P95 03736 filed Dec. 22, 1995.

This invention relates to novel racemic and optically active trans apovincaminic acid ester derivatives of formula

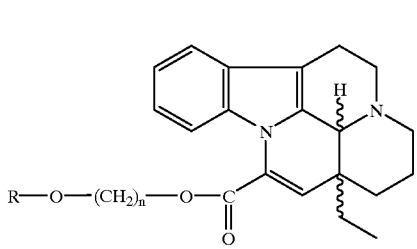

(I)

wherein
R is hydrogen or a

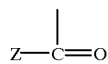

group, wherein Z is $C_{1-4}$ alkyl, optionally substituted aryl, aralkyl, heteroaryl or 14-eburnameninyl group; and
n is an integer of 2, 3 or 4
as well as their therapeutically acceptable salts and pharmaceutical compositions containing these compounds. Furthermore, the invention relates to a process for the preparation of the above compounds and compositions.

The compounds according to the invention are new and possess valuable biological activity. Under in vitro conditions they show a significant antioxidant (lipid peroxidation inhibitory) effect. Under in vivo conditions, they exert a remarkable antiischemic and antiamnesic action.

Accordingly, the invention relates also to a method of treatment, which comprises administering a therapeutically active amount of a compound of formula (I) or a therapeutically acceptable salt thereof to a patient to be treated. In the formula (I):

In the meaning of R: Z a $C_{1-4}$ alkyl group is a straight or branched chain saturated or unsaturated group such as e.g. methyl, ethyl, n-propyl, isopropyl, n-butyl, sec.-butyl, tert.-butyl, isobutyl, vinyl, propenyl group and the like; as aryl group Z may be e.g. phenyl group; as aralkyl group, it may be a benzyl, diphenylmethyl group or the like; as heteroaryl group it may be a five-, six- or seven-membered cyclic group containing identical or different heteroatoms, e.g. nitrogen, oxygen or sulfur atom, such as e.g. pyrryl, furyl, thienyl, pyridyl, pyranyl, pyrazolyl, imidazolyl, pyrimidinyl, morpholinyl groups or the like.

Substituents of the above aryl, aralkyl and heteroaryl groups may be: halogens such as fluorine, chlorine or bromine; $C_{1-4}$ alkyl or $C_{1-4}$ alkoxy groups; as well as hydroxyl, nitro, amino, cyano, trifluoromethyl groups or the like.

The therapeutically acceptable salts of compounds of formula (I) of the invention may be acid addition salts or quaternary salts.

Apovincaminic acid derivatives of formula (II) used as starting substances can be prepared by the acidic treatment of an appropriate hydroxyimino octahydroindolo[2,3-a]quinolizine derivative as described in the British patent specification No. GB 2,124,214.

There are compounds known from the literature which are structurally related to the compounds of the formula (I). Esters of trans apovincaminic acid with antiinflammatory, anticonvulsive, antiparkinsonian and antiatherosclerotic effects are described in the Hungarian patent specification No. 186,891. Antihypoxic or vasodilatory apovincaminic acid derivatives bearing various side chains are disclosed in the Hungarian patent specification No. 187,733.

Contrary to the above substances known from the literature, the new trans apovincaminic acid ester derivatives possess significant antioxidant, antiamnesic and antiischemic effects.

The continuous preservation of blood circulation is required for a normal functioning of the central nervous system (CNS) since this ensures a suitable supply of the extreme glucose and oxygen demand of brain tissue.

Due to ischemia and reperfusion, cognitive functions are injured: both reversible and irreversible damage may occur depending on the severity and duration of the ischemia. The injuries of structure and function of the neuronal cell membranes can lead to death of the neuron.

Several pathologic processes such as formation of free radicals may occur as a consequence of the ischemia. The formation of free radicals leads to the oxidation of unsaturated fatty acids (lipid peroxidation), which are important components of the membranes. This is a less specific cell-destroying process altering or damaging the biomolecules. Thus, functions of various levels of cells, organs or the whole organism may be injured.

Free radical reactions likely play a causal role in the pathogenesis of several ischemia-induced injuries such as ischemic intestinal diseases, myocardial ischemia, haemorrhagic shock, cerebrovascular function disturbances accompanied by ischemia, ischemic liver injury, renal ischemia and the like.

Due to their lipid peroxidation-inhibiting effect, antioxidant compounds assure protection against injuries induced by free radicals under ischemic conditions. Thus, antioxidants as antiischemic compounds can be useful in the treatment of the above pathological pictures.

In Vitro Tests for Investigation of the Antioxidant Effect

The antioxidant effect was studied by using two methods.
1. Effect on the NADPH-Induced Lipid Peroxidation in Brain Microsomes J. M. Braughler et al.: Novel 21-Amino Steroids as Potent inhibitors of Iron-dependent Lipid Peroxidation [J. Biol. Chem. 262. 10438–10440 (1987)].

T. J. Player and A. A. Horton: Enzyme Lipid Peroxidation in the Microsomal Fraction of Rat Brain [J. Neurochem. 37, 422–426 (1981)].

Male Hannover-Wistar rats with a body weight of 150–250 g were used for the preparation of microsomes. After decapitation, the whole brain was removed and homogenized in a 10-fold volume of ice-cold 0.25 M saccharose solution. The homogenate was centrifuged in a Hitachi CR 26H equipment at 15000 g at 4° C. for 10 minutes, then the supernatant was collected and centrifuged in a Hitachi SCP 85H apparatus at 78000 g at 4° C. for 60 minutes. After suspending the precipitate in 0.15 M KCl solution, the protein content of the obtained solution was determined and then adjusted to 10 mg/ml concentration. The microsome thus obtained was frozen in a dry iceacetone mixture and stored at −70° C. until use. The components of the incubation mixture were: 50 mM TRIS-HCl (pH 6.8), 0.2 mM FeCl$_3$, 1 mM KH$_2$PO$_4$, 0.5 mM ADP, 0.2 mg of microsomes as well as the compound to be tested. The incubation was carried out with a final volume of 1 ml and with an incubation time of 20 minutes at a temperature of 37° C. The lipid peroxidation was induced by adding 0.4 mM NADPH. (The blank samples did not contain NADPH.) The reaction was stopped by adding 0.375 ml of a stopping solution containing trichloroacetic acid of 40% and 5 M HCl in a 2:1 ratio.

The formation of malondialdehyde was determined by using thiobarbituric acid. After stopping the reaction, 1 ml of 1% thiobarbituric acid solution each was weighed to the samples, which were then placed in a water bath of about 100° C. for 10 minutes. Subsequently, the samples were centrifuged at 2000 g in a Janetzki K70 apparatus at 4° C. for 10 minutes. The absorbance values of the colored supernatant were measured at 535 nm in a Hitachi 150-20 spectrophotometer. Malondialdehyde bis(diethylacetal) was used as reference compound.

2. Effect on the Fe$^{2+}$-Induced Lipid Peroxidation in Brain Homogenate

After decapitating Hannover-Wistar rats weighing 150–220 g each, the whole brain was homogenized in 9 volumes of ice-cold Krebs-Ringer's buffer containing 15 mM HEPES, (4-(2-hydroxyethyl)-1-piperazinylethanesulfonic acid) (pH 7.4), 140 mM NaCl$_7$ 3.6 mM KCl, 1.5 mM CaCl$_2$, 0.7 mM MgCl$_2$, 1.4 mM KH$_2$PO$_4$ and 10 glucose. Then the protein content of the solution was determined and adjusted to 10 mg/ml concentration.

After adding the inhibitory agent to be tested in a volume of 5 µl to 200 µl of the homogenate, the incubation mixture was incubated at 37° C. for 20 minutes. The Fe$^{2+}$-induced lipid peroxidation was accomplished by adding 5 µl of 8 mM Fe$_2$(NH$_4$)$_2$(SO$_4$)$_2$ solution. After passing of the incubation time, the reaction was stopped by adding 1 ml of a stopping solution containing 0.8 M HCl and 12.5% trichloroacetic acid, then the samples were centrifuged at 2000 g in a Janetzki K70 apparatus at 4° C. for 10 minutes.

To a 0.5 ml portion of the supernatant, 1 ml of 1% thiobarbituric acid solution was added, then the samples were placed in a water bath of 100° C. for 20 minutes. The color intensity developed was determined at 535 nm with a Hitachi 150-20 spectrophotometer by using malondialdehyde bis(diethylacetal) as reference compound.

On the basis of the concentration/effect correlations of the tested compounds the IC$_{50}$ values were determined, these results are indicated in Table 1 for both methods.

TABLE 1

| Compound No. | Example No. | AEI (IC$_{50}$ µM) | ANI (IC$_{50}$ µM) |
|---|---|---|---|
| 2705279 | 2 | 6.3 | 4.8 |
| 1010885 | 1 | 9.7 | 15.5 |
| 1010962 | 8 | 7.5 | 5.7 |
| 1010960 | 6 | 7.4 | 5.7 |
| 1010961 | 7 | 5.9 | 5.3 |
| 1011005 | 9 | 10.3 | 11.9 |
| 2705283 | 3 | 11.2 | 6.8 |
| 2705284 | 4 | 20.4 | 6.8 |
| 1011008 | 10 | 6.0 | 21.2 |
| 1010887 | 13 | 12.6 | 7.2 |
| 1010886 | 18 | 7.6 | 7.7 |
| 1011038 | 16 | 8.4 | 8.7 |
| 1011036 | 14 | 7.7 | 9.3 |
| 1011037 | 15 | 3.2 | 11.4 |
| 1011047 | 17 | 5.9 | 16.1 |
| Idebenone |  | 1.2 | 18.9 |
| Vitamin E |  | 406.3 | 12.1 |
| Silymarin |  | 191.0 | 54.9 |

It can an be seen from the data of Table 1 that each of compounds according to the invention tested exerted an antioxidant (lipid peroxidation inhibitory) activity. The antioxidant effect was investigated both in an enzymatic (NADPH-induced, AEI) and in a non-enzymatic (Fe$^{2+}$-induced, ANI) lipid peroxidation test. The level of the antioxidant activity of the compounds was characterized by their IC$_{50}$ values. The cerebroprotectively active idebenone, the native antioxidant vitamin E (DL-α-tocopherol) and the hepatoprotective silymarin were used as reference compounds.

Based on the data of Table 1, the tested compounds showed a much higher activity in the inhibition of the NADPH-(enzymatically)induced lipid peroxidation than the reference compounds, as shown by their much lower IC$_{50}$ values than the IC$_{50}$ values of DL-α-tocopherol or silymarin are. Out of the compounds proved to be very effective, the antioxidant effect of the compounds Nos. 2705279, 1010961, 1011008, 1011037 and 1011047 was comparable to that of idebenone. The compounds Nos. 1010885, 1010962, 1010960, 1011005, 1010887, 1010886, 1011038, 1011036 and 2705283 inhibit the NADPH-induced lipid peroxidation about 20 times as strongly as silymarin does.

An overwhelming majority of the compounds listed in Table 1 showed a much stronger inhibitory effect on the Fe$^{2+}$ (non-enzymatically) induced lipid peroxidation than the reference compounds. The compounds Nos. 2705279, 2705283, 2705284, 1010962, 1010960, 1010961, 1010887, 1010886, 1011038 and 1011036 proved to be particularly active since each of them was about twice as active as idebenone or DL-α-tocopherol. The compounds Nos. 1011005 and 1011037 have an effect similar to that of DL-α-tocopherol. Compound Nos. 1010885 and 1011047 inhibit the Fe$^{2+}$ ion-induced lipid peroxidation more strongly than idebenone. The antioxidant activity of the compound No. 1011008 also exceeded that of silymarin.

It can be stated on comparison of the data obtained in both in vitro tests that the compounds Nos. 2705279, 1010962, 1010960, 1010961, 1010886, 1011038 and 1011036 very significantly inhibit the lipid peroxidation induced in different ways (by Fe$^{2+}$ ions or NADPH) namely, the IC$_{50}$ values of these compounds proved to be below 10 µM. Since none of the reference compounds could exert such an action on both tests (namely, they inhibited the NADPH- or Fe$^{2+}$ ion-induced lipid peroxidation to a different grade), the compounds according to the invention can be considered to be more effective than the reference compounds.

Each of the compounds investigated possess a significant antioxidant effectivity since they are capable to inhibit lipid peroxidation elicited by free radicals formed in Fenton's reaction (catalyzed by Fe$^{2+}$) or during the functioning of NADPH-cytochrome c reductase enzyme.

Abbreviations

NADPH: nicotinamide-adenine dinucleotide phosphate, reduced form
TRIS: tris(hydroxymethyl)aminomethane
ADP: adenosine-5'-diphosphate Idebenone: 6-(10-hydroxydecyl)-2,3-dimethoxy-5-methyl-1,4-benzoquinone DL-α-tocopherol: 2,5,7,8-tetramethyl-2-(4',8',12'-trimethyltridecyl)-6-chromanol Ellagic acid: 2,3,7,8-tetrahydroxy[1]benzopyrano[5,4,3-cde][1]benzopyran-5,10-dione Silymarin: silybinin+silydianin+silychristin AEI: enzymatically (NADPH-) induced lipid peroxidation test ANI: non-enzymatically ($Fe^{2+}$) induced lipid peroxidation test In Vitro Tests Used for Investigating the Antiischemic and Antiamnesic Effects 1. Antiischemic Effect (On Bilateral Artery Ligation Model)

N. Himori et al.: Cerebral ischemia model with conscious mice involvement of NMDA receptor activation and derangement of learning and memory ability [J. Pharmacol. Meth. 23, 311–327 (1990)].

Carotid arteries of mice (weighing 30 to 32 g each) were exposed bilaterally under anaesthesia by 450 mg/kg of intraperitoneal (i.p.) chloral hydrate. The sympathetic and vagal nerves were separated and a loose ligation was bilaterally placed below the carotid arteries. Both ends of the ligation were led out on the back, behind the ears. Next day, in conscious state both ends of the ligation were pulled resulting in the stopping of blood supply through the carotid arteries. This was maintained for 5 minutes, then released to provide the reperfusion. The number of animals died during the 5-minute period and the following 24 hours were registered. The calculation of significance was performed by the $chi^2$ test. The pre-treatment with the compound was carried out intraperitoneally (i.p.) 30 minutes before the ligation.

The effects of 2 mg/kg i.p. doses of the compounds on the mortality induced by the bilateral artery ligation are shown in Table 2.

TABLE 2

| Compound No. | Example No. | Mortality % |
|---|---|---|
| 2705279 | 2 | 10 |
| 1010885 | 1 | 60 |
| 1010960 | 6 | 20 |
| 1010961 | 7 | 60 |
| 1010962 | 8 | 40 |
| 1011005 | 9 | 70 |
| 1010887 | 13 | 30 |
| 1010886 | 13 | 30 |
| 1011036 | 14 | 50 |
| 1011037 | 15 | 50 |
| 1011038 | 16 | 60 |
| 1011047 | 17 | 50 |
| Idebenone | | 40 |
| Vitamin E | | 70 |
| Control | | 70 |

$ED_{50}$ values of the reference compounds as well as of the most effective compound administered i.p. are shown in Table 3.

TABLE 3

| Compound | ED50 i.p. (mg/kg) |
|---|---|
| Idebenone | 4.50 (0.96–9.38) |
| Vitamin E | 17.80 (8.46–41.8) |
| 2705279 | 0.76 (0.2–1.27) |

The in vivo biological activity of compounds exerting a significant antioxidant effect ($IC_{50}<10$ μM) under in vitro conditions was investigated on the bilateral artery ligation-induced cerebral ischaemia model. The transient dramatic decrease in the cerebral blood supply, then the starting of reperfusion after stopping the ligation leads to the formation of extremely toxic oxygen free radicals (superoxide radical, hydrogen peroxide). Compounds having antioxidant properties are very effective in the protection against the toxic effects of radicals liberated. A 5-minute bilateral ligation of the carotid artery results in 70% mortality. Two mg/kg i.p. doses of the most active compounds of the invention (2705279, 1010960, 1010887, 1010886) lo decrease this mortality to 10–30%; whereas known antioxidants such as idebenone or vitamin E used as reference compounds are less active in the same dose. The excellent activity of the compound No. 2705279 found to be most active, is even more striking when the $ED_{50}$ values of the compounds are compared. [$ED_{50}$ is the dose (as mg/kg) diminishing the mortality by 50% in comparison to the untreated is control group]. The i.p. $ED_{50}$ value of idebenone is 4.5 mg/kg whereas this value is 0.76 mg/kg i.p. for the compound No. 2705279. The antiischemic effect of this compound can be measured after oral administration, too. It was shown in other experiments that this compound is active not only on a global ischemic model involving the whole brain substance but also on the so called "focal" ischemia models elicited in one well-determined area of the brain.

The antiamnesic action of compounds according to the invention was confirmed by the following experiment.

2. Diazepam-Induced Anterograde Amnesia

C. L. Broekkamp et al.: The comparative effects of benzodiazepines, progabide and PK 9084 on acquisition of passive avoidance in mice [Psychopharmacology (Berlin) 83, 122–125 (1984)].

The memory test was accomplished on NMRI mice weighing 25 to 28 g each by using the passive avoidance, a method based on the genetically determined nyctophilic behavior of rodents. During the learning period, the pre-selected animals (mice entering the dark space from the illuminated space within 30 seconds) were placed in an illuminated space. After entering the dark space, the animal received an electric shock (1 mA for 3 minutes) onto its planta within 30 seconds, then the time until entry to the dark space (latency period) was registered. After 24 hours, the animals were placed again in the illuminated space and the time until crossing over to the dark space (retention time=T with a time limit of 300 seconds) was measured. For inducing an anterograde amnesia, the animals were treated intraperitoneally with 3 mg/kg of diazepam 30 minutes before learning. The compounds were administered orally in 0.1 or 10 mg/kg doses, respectively 1 hour before learning. The percentage value of the protective effect (P%) was calculated by means of the following formula and is shown in Table 4.

$$P\% = \frac{T_{treated+DIA} - T_{placebo+DIA}}{T_{placebo} - T_{placebo+DIA}} \times 100$$

TABLE 4

Effect of the compounds in diazepam-induced anterograde amnesia model

| Compound No. | Example No. | Inhibition of the diazepam-induced amnesia % | |
|---|---|---|---|
| | | 0.1 mg/kg p.o. | 10.0 mg/kg p.o. |
| 1010885 | 1 | 74 | 65 |
| 2705279 | 2 | 79 | 119 |
| 1010960 | 6 | 0 | 0 |
| 1010961 | 7 | 3 | 15 |

TABLE 4-continued

Effect of the compounds in diazepam-induced anterograde amnesia model

| Compound No. | Example No. | Inhibition of the diazepam-induced amnesia % | |
|---|---|---|---|
| | | 0.1 mg/kg p.o. | 10.0 mg/kg p.o. |
| 1010962 | 8 | 16 | 4 |
| 1010887 | 13 | 50 | 56 |
| 1010886 | 18 | 72 | 44 |
| 1011038 | 16 | 64 | 24 |
| 1011036 | 14 | 23 | 16 |
| Vinpocetine | | 0 | 123 |

Compounds possessing antioxidant activity exert significant protective action in events of cerebral ischemia [transient ischemic attack (TIA), stroke], where the injury of learning and memory may occur in addition to neurological symptoms of various severity. The antiamnesic effect of compounds according to the invention was studied on diazepam-induced anterograde amnesia model by using as reference compound vinpocetine, which is structurally similar and is being used in the clinical practice. Active compounds were found both among trans-α-ethyl as well as trans-β-ethyl apovincaminic acid derivatives. The compounds Nos. 2705279, 1010886, 1011038 and 1010887 proved to be particularly effective. The most active substance was 2705279 exhibiting a significant protective effect in both doses used and an activity by far exceeding that of vinpocetine. The antiamnesic effect of 2705279 was confirmed also on other amnesia models: it showed a dose-dependent protective action in an oral dose range between 0.1 and 10 mg/kg on electroshock-induced retrograde amnesia model; and protected against the ischemia-induced injury of memory in an oral dose range between 1 and 10 mg/kg. Its antiamnesic activity could well be measured in rats, too.

SUMMARY

The novel trans apovincaminic acid derivatives according to the invention possess significant antioxidant and antiischemic effects. The antioxidant activity of compound No. 2705279 found to be most effective surpasses both in vitro and in vivo that of idebenone or vinpocetine, respectively employed as reference substances. In addition to their antioxidant and antiischemic effects, the compounds according to the invention exhibit also an antiamnesic effect of various strength. The compound No. 2705279 is most active in this field, too.

Due to their antioxidant, antiischemic and antiamnesic effects, the compounds according to the invention are useful for the treatment of pathologic pictures, where free radicals play a role either in the acute period of a disease or in the development of late sequels. These are: cerebrovascular ischemic injury, stroke, apoplexia, cerebral or spinal traumas, subarachnoidal or intracerebral heamorrhages as well as various neurodegenerative diseases such as Alzheimer's disease. Due to their antiischemic effect, the compounds may be useful to treat not only ischemic injury of the brain but also of other organs such as e.g. liver, heart or muscles.

In the above clinical syndromes the expected therapeutical doses of the compounds of the invention are between 0.1 and 40 mg/kg of body weight, which are administered daily once or in several divided doses in oral or parenteral route.

According to the invention the novel trans apovincaminic acid ester derivatives of formula (I) as well as their therapeutically acceptable salts can be prepared by transesterifying a racemic or optically active trans apovincaminic acid ester derivative of formula

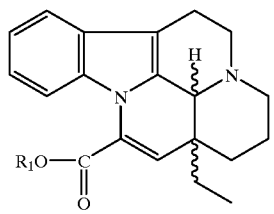

(II)

wherein $R_1$ represents $C_{1-4}$ alkyl group, in a suitable glycol in the presence of a basic catalyst; and, if desired, acylating the so obtained compound of formula (I) wherein R is hydrogen, and/or, if desired, resolving the racemic compound of formula (I), and/or, if desired, converting the compound of formula (I) to therapeutically acceptable salts thereof.

Hereinafter, the preparation of the novel therapeutically active compounds of the invention will be described in detail.

In the process of the invention to prepare compounds of formula (I), wherein R stands for hydrogen, a compound of formula (II) is subjected to transesterification. This reaction is carried out in excess of the transesterifying alcohol, such as in an appropriate glycol, preferably ethylene glycol, suitably under anhydrous conditions in the presence of catalytic amount of a strong base. As a base alkaline metal hydrides or alkaline metal alkoxides, suitably tertiary alkoxides, preferably e.g. potassium tertiary butoxide may be used. The transesterification is accomplished at a temperature range between 80° C. and 140° C., advantageously between 110° C. and 120° C. If desired, the product obtained after carrying out the reaction is employed in the next reaction step without isolation; or if desired, it can be recovered in such a way that the reaction mixture is poured into water and after filtration, if desired, the precipitate is purified by recrystallization; or, after dilution with water, the reaction mixture is extracted with an inert water-immiscible organic solvent such as dichloromethane or chlorobenzene then, the product is isolated by evaporation or salt formation. Compounds of formula (I), wherein R is hydrogen can be transformed by acylation to compounds of formula (I), wherein R means

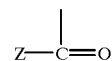

group.

The acylating reaction may be carried out by any organic carboxylic acid containing the appropriate acyl group; or by using a reactive derivative thereof such as e.g. an acyl halide, preferably acyl chloride or acid anhydride or the like in a known manner, if desired, in the presence of an acid binding agent.

On carrying out the acylation with an appropriate carboxylic acid, the reaction is accomplished in an inert organic solvent, e.g. a dipolar aprotic solvent such as dimethylformamide (DMF), dimethyl sulfoxide (DMSO), acetonitrile or the like in the presence of a condensing agent. Useful condensing agents are e.g. carbodiimide derivatives such as dicyclohexylcarbodiimide, or carbonyldiimidazole. The reaction is carried out at a temperature from 0° C. to 40° C., preferably at room temperature.

If the acylation is accomplished with an acyl halide, suitably acyl chloride, the reaction is carried out in an inert organic solvent such as an aliphatic or cyclic ether, e.g. diethyl ether or tetrahydrofuran (THF); or in a chlorinated hydrocarbon, e.g. chloroform; or in an aromatic hydrocarbon, e.g. benzene, chlorobenzene or toluene; or in an organic base, e.g. pyridine, preferably in the presence of an acid binding agent. Organic bases, e.g. pyridine, employed in the reaction can simultaneously play both the role of solvent and acid binding agent.

Compounds of formula (I), wherein R stands for a

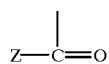

group, can be recovered from the solvent in such a manner that, after removing the solvent or if desired the excess of reagent and the acid binding agent, the residue obtained is dissolved in a mixture of water and a water-immiscible solvent such as ethyl acetate, chloroform, dichloromethane, benzene, diethyl ether or the like then, if desired, the pH value of the mixture is adjusted to slightly alkaline (pH 8 to 9) by adding aqueous ammonium hydroxide solution or aqueous alkaline metal hydrogen carbonate solution and the phases are separated. The organic phase is washed with water, dried and the solvent is removed under reduced pressure to obtain the compound desired.

If desired, the compounds of formula (I) according to the invention can be converted to quaternary salts. A slightly higher than equimolar amount of an alkyl halide, preferably chloride, bromide, iodide or an alkyl sulfate are preferably used for the quaternary salt formation. This reaction may be carried out in an inert organic, dipolar aprotic solvent.

If desired, the compounds of formula (I) of the invention can be converted to their acid addition salts in a know manner by using any acid useful for the formation of therapeutically acceptable acid addition salts.

If desired, the compounds of formula (I) prepared by the process according to the invention or salts thereof may be subjected to additional purifying operations, e.g. recrystallization. The scope of solvents useful for recrystallization depends on the dissolution and crystallization properties of the compounds to be recrystallized.

The novel trans apovincaminic acid ester derivatives of formula (I) according to the invention may be racemic or optically active. By using optically active compounds of formula (II) as starting substances, optically active compounds of formula (I) are obtained; whereas racemic compounds of formula (II) employed as starting substances result in racemic compounds of formula (I). From the racemates of formula (I), the optically active compounds can be obtained by resolving them in a manner known per se.

The new racemic or optically active trans apovincaminic acid ester derivatives of formula (I) or salts thereof can be converted to pharmaceutical compositions by mixing them with non-toxic, inert solid or liquid carriers and/or other auxiliaries commonly used in the therapy for parenteral or eternal administration. Useful carriers are e.g. water, gelatine, lactose, starch, pectin, magnesium-stearate, stearic acid, talc, vegetable oils, such as peanut oil, olive oil and the like. The active ingredient may be formulated in any usual pharmaceutical composition, particularly solid composition, e.g. tablet, dragee, capsule, suppository and the like. The amount of the solid carrier may be varied between broad limits, preferably it is between about 25 mg and 1 g. Optionally, the compositions may contain also commonly used other pharmaceutical auxiliaries, e.g. stabilizers, preservatives, wetting agents, surfactants, emulsifying agents and the like. The compositions can be prepared in a known manner by any usual pharmaceutical technology and, if desired, they may be subjected to other usual operations, e.g. sterilization.

The invention is illustrated in detail by the aid of the following non-limiting Examples.

EXAMPLE 1

Preparation of (−)-trans apovincaminic acid 2-hydroxyethyl ester(3β,16α)

After stirring 15 g (0.045 mol) of (−)-trans apovincaminic acid methyl ester(3β,16α) in 300 ml of ethylene glycol in the presence of 1 g of potassium tert.-butoxide at 120° C. for 5 hours and then cooling the reaction mixture to room temperature. The mixture is poured into 1 liter of ice-water, the crystalline precipitate is filtered, washed twice with 50 ml of water each and dried to give 15.9 g (97% yield) of title product, m.p.: 82–87° C.

$[\alpha]_D^{20}$=−138.7° (c=0.2; chloroform).

$^1$H-NMR (CDCl$_3$) δ: 0.65 (3H), t, C$\underline{H}_3$CH$_2$); 0.66–3.2 (14H, m, skeletal protons, OH); 3.85 (2H, m, HO—C$\underline{H}_2$); 4.43 (2H, m, C$\underline{H}$—O—C=O); 6.35 (1H, s, H-15); 7.00–7.55 (4H, m, aromatic protons).

Analysis:

Calculated for C$_{22}$H$_{26}$N$_2$O$_3$ (molecular weight 366.44):

|  |  |  |  |  |  |  |
|---|---|---|---|---|---|---|
|  | C | 72.10; | H | 7.15; | N | 7.65%; |
| found | C | 71.89 | H | 7.15; | N | 7.62%. |

EXAMPLE 2

Preparation of (−)-trans apovincaminic acid 2-acetoxyethyl ester(3β,16α)monohydrochloride To a solution containing 3.66 g (0.01 mol) of (−)-trans-apovincaminic acid 2-hydroxyethyl ester(3β,16α) in 50 ml of anhydrous pyridine, 5 ml (0.052 mol) of acetic acid anhydride are dropwise added, the reaction mixture is allowed to stand at room temperature overnight, then evaporated to dryness under reduced pressure. After dissolving the evaporation residue in a mixture of 100 ml of ethyl-acetate, 30 ml of water and 50 ml of saturated sodium hydrogen carbonate solution, the phases are separated. The organic layer is washed 3 times with 20 ml of water each and dried over anhydrous sodium sulfate.

The solution of the evaporation residue in 30 ml of isopropanol is acidified to pH 4 by adding ethanolic hydrogen chloride solution, left to stand in a refrigerator overnight, then the crystalline precipitate is filtered and dried to obtain 2.8 g (62%) of title product, m.p.: 179–189° C.

$[\alpha]_D^{20}$=−18.9° (c=0.2; methanol).

$^1$H-NMR (CDCl$_3$) δ: 0.75 (3H, t, C$\underline{H}_3$CH$_2$); 2.1 (3H, s, CH$_3$CO); 4.28 (1H, s, H-3); 6.28 (1H, s, H-1 5); 4.30–4.70 (4H, m, —OCH$_2$CH$_2$CH$_2$O—); 7.05–7.60 (4H, m, aromatic protons).

EXAMPLE 3

Preparation of (−)-trans apovincaminic acid 2-(2-thiophenoyloxi)ethyl ester(3β,16α)monohydrochloride To a solution prepared at room temperature from 3.66 g (0.01 mol) of (−)-trans apovincaminic acid 2-hydroxyethyl ester(3β,16α) in 20 ml of anhydrous pyridine, 4.8 ml (0.045 mol) of thiophene-2-carboxylic acid chloride are dropped, the reaction mixture is allowed to stand for 24 hours and then evaporated to dryness under reduced pressure. After adding 100 ml of dichloromethane and 20 ml of water to the evaporation residue, the pH is adjusted to 9 by adding 20 ml of saturated sodium hydrogen carbonate solution. After separation of the phases, the organic phase is washed with water and dried over anhydrous sodium sulfate. After filtration, the solution is evaporated to dryness under reduced pressure, the residue is dissolved in 50 ml of isopropanol and the pH is adjusted to 4 by adding ethanolic hydrogen chloride solution. After standing in a refrigerator overnight, the solution is filtered and the crystalline precipitate is washed with cold isopropanol to give 2.9 g of title product (yield 57%).

m.p.: 178–183° C.; $[\alpha]_D^{20}$=−113.9° (c=0.2; chloroform).

EXAMPLE 4
Preparation of (−)-trans apovincaminic acid 2-(4-nitrobenzoyloxy)ethyl ester(3β,16α)

To a solution prepared at room temperature from 3.66 g (0.01 mol) (−)-trans apovincaminic acid 2-hydroxyethyl ester(3β,16α) in 20 ml of anhydrous pyridine, 4.2 g (0.0225 mol) of 4-nitrobenzoyl chloride are added and the reaction mixture is allowed to stand overnight. After diluting the reaction mixture with 150 ml of ethyl acetate, 50 ml of water and 3 ml of concentrated aqueous ammonium hydroxide solution are added. The phases are separated then the organic phase is washed 4 times with 25 ml of water each and dried over anhydrous sodium sulfate. After filtration the solution is evaporated to dryness under reduced pressure, the oily residue is dissolved in 50 ml of hot isopropanol, clarified by activated charcoal and after filtration the solution is left to stand for a few hours. The crystalline precipitate is filtered, washed with 10 ml of isopropanol and dried to yield 2.6 g (58%) of title product, m.p.: 139–142° C.; $[\alpha]_D^{20}$=−86.7° (c=0.2; chloroform).

EXAMPLE 5
Preparation of (−)-trans apovincaminic acid 2-(nicotinoyloxy)ethyl ester dihydrochloride(3β,16α)

To a solution containing 2.4 g (0.0065 mol) of (−)-trans apovincaminic acid 2-hydroxyethyl ester(3β,16α) in 20 ml of anhydrous pyridine, 2.15 g (0.015 mol) of nicotinoyl chloride dissolved in 10 ml of pyridine are added dropwise, the reaction mixture is stirred at room temperature for 3 hours, then evaporated to dryness under reduced pressure. After dissolving the evaporation residue in a mixture of 150 ml of ethyl acetate and 50 ml of saturated sodium hydrogen carbonate solution the phases are separated. The organic layer is twice washed with 20 ml of water each and dried over anhydrous sodium sulfate. After filtering, the solution is evaporated to dryness under reduced pressure, the evaporation residue is dissolved in 30 ml of isopropanol and the solution is acidified to pH 4 by adding ethanolic hydrogen chloride solution. After evaporation to dryness under reduced pressure the residue is crystallized from 50 ml of ethyl acetate to give 1.30 g (36%) of the title compound, m.p.: 158–164° C.; $[a]_D^{20}$=−69.5° (c=0.2; chloroform).

Analysis:

Calculated for $C_{28}H_{29}N_3O_4 \cdot 2HCl$ (molecular weight: 544.47):

|  | C | 61.76; | H | 5.73; | N | 7.71 | Cl | 13.02%; |
|---|---|---|---|---|---|---|---|---|
| found: | C | 61.73; | H | 6.05; | N | 7.69; | Cl | 12.90%. |

EXAMPLE 6
Preparation of (−)-trans apovincaminic acid 2-(benzoyloxy)ethyl ester(3β,16α)hydrochloride To a solution of 4.4 g (0.012 mol) of (−)-trans apovincaminic acid 2-hydroxyethyl ester(3β,16α) in 60 ml of chlorobenzene, 1.83 g (0.018 mol) of triethylamine and 2.5 g (0.018 mol) of benzoyl chloride are added. The mixture is stirred at 40° C. for 30 minutes, then made alkaline to pH 8 by adding 15 ml of 10% sodium hydrogen carbonate solution. After separation, the organic phase is twice washed with 20 ml of water each and dried over anhydrous magnesium sulfate. After filtering off the drying agent and washing it twice with 3 ml of chlorobenzene each, a solution of hydrogen chloride in dioxane is added up to pH 3–4, then the crystalline precipitate is filtered at 0° C., thoroughly triturated with cold acetone and filtered to obtain 4.8 g (79%) of title product, m.p.: 216–217.5° C.; $[\alpha]_D^{20}$=−86.6° (c=1; methanol).

EXAMPLE 7
Preparation of (−)-trans apovincaminic acid 2-(4-chlorobenzoyloxy)ethyl ester(3β,16α)methanesulfonate After dissolving 4.4 g (0.012 mol) of (−)-trans apovincaminic acid 2-hydroxyethyl ester(3β,16α) in 60 ml of dichloromethane, 1.83 g (0.018 mol) of triethylamine and 3.15 g (0.018 mol) of 4-chlorobenzoyl chloride are added and the reaction mixture is stirred at 40° C. for 30 minutes. After cooling down to 10° C., 25 ml of water are added and the pH value of the mixture is adjusted to 8 by adding 15 ml of 10% sodium hydrogen carbonate solution. After separation the organic phase is twice washed with 20 ml of water each and dried over anhydrous magnesium sulfate. After filtration of the drying agent and washed twice with 5 ml of dichloromethane each, the organic phase is evaporated until it becomes free of solvent. The residue is dissolved in 35 ml of acetone and acidified to pH 4 by adding methanesulfonic acid. The crystalline precipitate is filtered at 0° C., washed with cold acetone and dried to give 5.85 g (81%) of title salt, m.p.:197–199° C.; $[\alpha]_D^{20}$=−73.3° (c=1; methanol).

EXAMPLE 8
Preparation of (−)-trans apovincaminic acid 2-(propionyloxyethyl)ester(3β,16α)hydrochloride To a solution containing 4.4 g (0.012 mol) of (−)-trans apovincaminic acid 2-hydroxyethyl ester(3β,16α) in 100 ml of chlorobenzene, 5.33 g (0.04 mol) of propionic acid anhydride and 1.4 g (0.014 mol) of trietylamine are added. After stirring the reaction mixture at 80° C. for 4 hours, 40 ml of chlorobenzene and the excess of propionic anhydride are distilled off under reduced pressure. After adding 25 ml of water to the residue at room temperature, the pH is adjusted to 8 by adding 20 ml of 10% sodium hydrogen carbonate solution. After separation, the organic phase is twice washed with 20 ml of water each and dried over anhydrous magnesium sulfate. The drying agent is filtered off and twice washed with 3 ml of chlorobenzene each. After evaporating the organic phase under reduced pressure until solvent-free, the residue is dissolved in 40 ml of acetone and acidified to pH 4 by adding a dioxane solution of hydrogen chloride. The crystals are filtered at 5° C., washed with acetone and dried to result in 4.2 9 (76%) of title hydrochloride, m.p.: 219–220° C.; $[\alpha]_D^{20}$=−111.9° (c=1; methanol).

EXAMPLE 9
Preparation of (−)-trans apovincaminic acid 2-(3,4,5-trimethoxybenzoyloxy)-ethyl ester(3β,16α)hydrochloride To a solution containing 5.1 g (0.014 mol) of (−)-trans apovincaminic acid 2-hydroxyethyl ester(3β,16α) in 80 ml of dichloroethane, 2 g (0.02 mol) of triethylamine and 4.6 g (0.02 mol) of 3,4,5-trimethoxybenzoyl chloride are added.

The mixture is stirred at 50° C. for 1 hour, then 50 ml of water are added at room temperature and the mixture is alkalinized to pH 8 by adding 20 ml of 10% sodium hydrogen carbonate solution. After separation, the organic phase is twice washed with 25 ml of water each and dried over anhydrous magnesium sulfate. After filtration of the drying agent and washing it twice with 5 ml of dichloroethane each, the filtrate is evaporated to dryness under reduced pressure, the residue is dissolved in 25 ml of ethyl acetate and acidified to pH 4 by a dioxane solution of hydrogen chloride. The crystalline precipitate is filtered at 10° C. and washed with acetone to give 6.2 g (76%) of title hydrochloride, m.p.: 191–194° C.; $[\alpha]_D^{20} = -96.2°$ (c=1; methanol).

EXAMPLE 10
Preparation of (−)-Bis-trans apovincaminic acid ethyleneglycol ester(3β,16β)dihydrochloride To a solution containing 5.1 g (0.014 mol) of (−)-trans apovincaminic acid 2-hydroxyethyl ester(3β,16α) in 100 ml of dichloroethane, 6 g (0.06 mol) of triethylamine then, under cooling 7.54 g (0.02 mol) of (−)-trans apovincaminic acid chloride hydrochloride are added and subsequently, the reaction mixture is stirred at room temperature for 2 hours. After adding to the mixture 50 ml of water and 20 ml of 10% sodium hydrogen carbonate solution up to pH 8 and separation, the organic phase is twice washed with 25 ml of water each, dried over anhydrous magnesium sulfate, filtered and washed twice with 5 ml of dichloroethane each. The organic layer is evaporated until solvent-free. The residue is dissolved in 60 ml of acetone and acidified to pH 3.5 by adding hydrogen chloride dissolved in dioxane. The crystalline precipitate is filtered at 5° C. and washed with acetone to obtain 6.55 g (63%) of title dihydrochloride.

m.p.: 222–225° C.; $[\alpha]_D^{20} = -131.5°$ (c=1; methanol).

EXAMPLE 11
Preparation of (−)-trans apovincaminic acid 2-(acetoxy)ethyl ester(3β,16α)methanesulfonate To a solution of 7.3 g (0.02 mol) of (−)-trans apovincaminic acid 2-hydroxyethyl ester(3β,16α) in 100 ml of dichloroethane, 2.2 g (0.022 mol) of triethylamine and 2.42 g (0.03 mol) of acetyl chloride are added. After stirring the reaction mixture at 50° C. for 15 minutes, then adding 50 ml of water at room temperature, it is alkalinized to pH 8 by adding 20 ml of 10% sodium hydrogen carbonate solution. After separation, the organic phase is twice washed with 25 ml of dichloroethane and dried over anhydrous magnesium sulfate. The drying agent is filtered, washed twice with 5 ml of dichloroethane each and the filtrate is evaporated under reduced pressure until solvent-free. The residue is dissolved in 40 ml of ethyl acetate and acidified to pH 3 with methanesulfonic acid. After filtering the crystalline precipitate at 0° C., washing with ethyl acetate and drying, 7.75 g (77%) of title salt are obtained, m.p.: 130–133° C.

$[\alpha]_D^{20} = -92.2°$ (c=1 methanol).

EXAMPLE 12
Preparation of (−)-trans apovincaminic acid 2-(acetoxy)ethyl ester(3β,16α)benzoesulfonate By following the procedure described in Example 11, the salt formation is carried out with benzenesulfonic acid instead of methanesulfonic acid, at a pH value of 3.5. The benzenesulfonate salt is obtained in a yield of 7.9 g (70%), m.p.: 180.5–183° C.; $[\alpha]_D^{20} = -90.3°$ (c=1; methanol).

EXAMPLE 13
Preparation of (+)-trans apovincaminic acid 2-hydroxyethyl ester(3α,16β)

A solution containing 16.88 g (0.05 mol) of /+/-trans apovincaminic acid methyl ester (3α,16β) in 335 ml of ethylene glycol is stirred with 1 g of potassium tert.-butoxide at 120° C. for 5 hours. After cooling to room temperature, the reaction mixture is slowly poured into 1 liter of ice-water. The precipitate is filtered, washed 3 times with 500 ml of water each and dried to give the title compound in a yield of 17.6 g (96%), m.p.: 85–90° C.; $[\alpha]_D^{20} = +131.20$ (c=1; chloroform).

EXAMPLE 14
Preparation of (−)-trans apovincaminic acid 2-(benzoyloxy)ethyl ester(3α,16β)hydrochloride By following the procedure described in Example 6, 4.4 g (0.12 mol) of (+)-trans apovincaminic acid 2-hydroxyethyl ester (3α,16β) are used instead of (−)-trans apovincaminic acid 2-hydroxyethyl ester (3α,16β), to obtain 4.7 9 (77%) of the title hydrochloride, m.p.: 217–219° C. $[\alpha]_D^{20} = +84.9°$ (c=1; methanol).

EXAMPLE 15
Preparation of (+)-trans apovincaminic acid 2-(4-chlorobenzoyloxy)-ethyl ester(3α,16β)methanesulfonate The procedure described in Example 7 is followed, but instead of 4.4 g (0.012 mol) of (−)-trans apovincaminic acid 2-hydroxyethyl ester(3β,16α), 4.4 g (0.012 mol) of (+)-trans apovincaminic acid 2-hydroxyethyl ester(3α, 16β) are used to result of the title salt, in a yield of 5.5 g (76%). m.p.: 199–200° C.

$[\alpha]_D^{20} = +73.3°$ (c=1; methanol).

EXAMPLE 16
Preparation of (+)-trans apovincaminic acid 2-(propionyloxy)ethyl ester(3α,16β)hydrochloride The procedure described in Example 8 is followed, but 4.4 g (0.012 mol) of (+)-trans apovincaminic acid 2-hydroxyethyl ester (3α,16βR) are used instead of 4.4 g (0.012 mol) of (−)-trans apovincaminic acid 2-hydroxyethyl ester(3β,16α), to obtain 4.35 g (79%) of the title hydrochloride, m.p.: 220–200° C.

$[\alpha]_D^{20} = +109.7°$ (c=1; methanol).

EXAMPLE 17
Preparation of (+)-trans apovincaminic acid 2-(3,4,5-trimethoxybenzoyloxy)ethyl ester(3α,16β)

The procedure described in Example 9 is followed, but 5.1 g (0.14 mol) of (+)-trans apovincaminic acid 2-hydroxyethyl ester (3α,16β) are used instead of 5.1 g (0.014 mol) of (−)-trans apovincaminic acid 2-hydroxyethyl ester(3β,16α), to obtain 6.2 g (76%) of title hydrochloride, m.p.: 192–195° C.

$[\alpha]_D^{20} = +95.3°$ (c=1; methanol).

EXAMPLE 18
Preparation of (+)-trans apovincaminic acid 2-(acetoxy)ethyl ester(3α,16β)hydrochloride To a solution of 7.3 g (0.02 mol) of (−)-trans-apovincaminic acid 2-hydroxyethyl ester (3α,16β) in 100 ml of dichloroethane, 2.2 g (0.022 mol) of triethylamine and 2.42 g (0.03 mol) of acetyl chloride are added. After stirring at 40° C. for 25 minutes and then adding 50 ml of water at room temperature, the pH is adjusted to 8 by adding 20 ml of 10% sodium hydrogen carbonate solution. After separation, the organic phase is twice washed with 25 ml of water each and dried over anhydrous magnesium sulfate. After filtration, the drying agent is twice washed with 5 ml of dichloroethane each and the filtrate is evaporated under reduced pressure until solvent-free. The residue is dissolved in 40 ml of ethyl acetate and acidified to pH 4 by adding dioxane solution of hydrogen chloride. The crystalline precipitate is filtered at 0° C., washed with ethyl acetate and dried to afford 6.95 g (78%) of the title hydrochloride, m.p.: 221–224.5° C.

$[\alpha]_D^{20}=+107.4°$ (c=1; methanol).

EXAMPLE 19

Preparation of racemic trans apovincaminic acid 2-hydroxyethyl ester hydrochloride The procedure described in Example 13 is followed, but, 16.8 g (0.05 mol) of racemic-trans apovincaminic acid methyl ester are used instead of 16.8 g (0.05 mol) of (+)-trans apovincaminic acid methyl ester (3α,16β) to give the title racemate hydrochloride in a yield of 17.4 g (95%), m.p.: 97–101° C.

EXAMPLE 20

Preparation of racemic trans apovincaminic acid 2-(acetoxy) ethyl ester hydrochloride The procedure described in Example 18 is followed, but 7.3 g (0.02 mol) of racemic trans apovincaminic acid 2-hydroxyethyl ester are used instead of 7.3 g (0.02 mol) of (+)-trans apovincaminic acid 2-hydroxyethyl ester (3α,16β), to give 7.1 g (80%) of the title hydrochloride, m.p.: 187–189° C.

EXAMPLE 21

Preparation of (-)-trans apovincaminic acid 3-hydroxypropyl ester(3β,16α)

The procedure described in Example 1 is followed, but 300 ml of propylene glycol are used instead of 300 ml of ethylene glycol. After pouring into water, the water-immiscible oil obtained is dissolved in 100 ml of dichloromethane and twice washed with 20 ml of water each. The organic layer is dried over anhydrous magnesium sulfate and filtered. The drying agent is twice washed with 5 ml of dichloromethane each and the filtrate is evaporated under reduced pressure until solvent-free. The title compound is obtained in a yield of 16.8 g in the form of a light-yellow viscous oil. The hydrochloride salt melts at 216–218° C. after recrystallization from acetone; $[\alpha]_D^{20}=-122.2°$ (c=1; methanol).

EXAMPLE 22

Preparation of (-)-trans apovincaminic acid 3-(acetoxy) propyl ester(3β,16α)hydrochloride The procedure described in Example 18 is followed, but 7.6 g (0.02 mol) of (-)trans apovincaminic acid 3-hydroxypropyl ester(3β,16α) are used, instead of 7.3 g (0.02 mol) of (+)-trans apovincaminic acid 2-hydroxyethyl ester (3α,16β), to result of the title hydrochloride, in a yield of 7.0 g (76%) m.p. :205–207° C.

$[\alpha]_D^{20}=-113.2°$ (c=1;methanol).

What is claimed is:

1. A trans compound of the formula

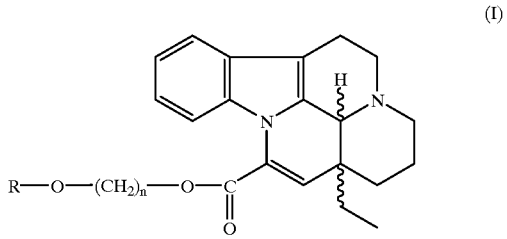

(I)

wherein
R is hydrogen or a Z—C=O group, wherein Z is a $C_{1-4}$ alkyl group, an optionally substituted aryl, aralkyl, 14-eburnameninyl or heteroaryl group where the heteroaryl group is a five, six or seven membered cyclic group containing identical or different heteroatoms selected from the group consisting of nitrogen, oxygen and sulfur; and
n is an integer of 2, 3 or 4
or a pharmaceutically acceptable salt thereof.

2. (-)-Trans apovincaminic acid 2-(acetoxy)ethyl ester (3β,16α) or a pharmaceutically acceptable salt thereof as defined in claim 1.

3. A pharmaceutical composition for inhibiting lipid peroxidation and for treating ischemia, amnesia or a neurodegenerative disease which comprises a therapeutically effective amount of a compound of the Formula (I) as defined in claim 1 or a pharmaceutically acceptable salt thereof in combination with a pharmaceutically acceptable inert carrier.

4. A method of inhibiting lipid peroxidation, and of treating ischemia, amnesia, or a neurodegenerative disease which comprises the step of administering to a mammalian subject in need of said treatment, a therapeutically effective amount of the compound of the Formula (I) as defined in claim 1 or a pharmaceutically acceptable salt thereof alone or in combination with a pharmaceutically acceptable inert carrier.

5. The trans compound defined in claim 1 wherein the heterocyclic group is pyrryl, furyl, thienyl, pyridyl, pyranyl, pyrazolyl, imidazolyl, pyrimidinyl, or morpholinyl.

6. A process for the preparation of a trans compound of the formula

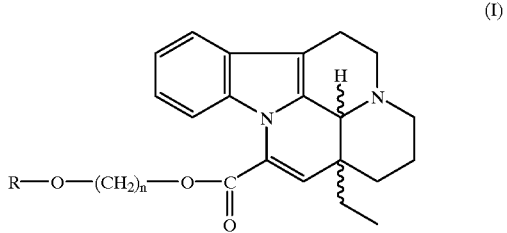

(I)

wherein
R is hydrogen or a

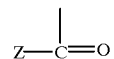

group, wherein Z is a $C_{1-4}$ alkyl group, or an optionally substituted aryl, aralkyl, 14-eburnameninyl or heteroaryl group where the heteroaryl group is a five, six or seven membered cyclic group containing identical or different heteroatoms selected from the group consisting of nitrogen, oxygen and sulfur; and n is an integer of 2, 3 or 4 or a pharmaceutically acceptable salt thereof, which comprises transesterifying a trans compound of the formula

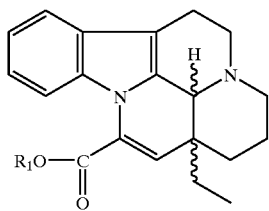

(II)

wherein $R_1$ is a $C_{1-4}$ alkyl group, in a glycol solvent in the presence of a basic catalyst; and, if desired, acylating a compound of formula (I) wherein R is hydrogen, or if desired, resolving a racemic compound of formula (I), or if desired, converting a compound of formula (I) to a therapeutically acceptable salt thereof.

7. The process for the preparation of a trans compound defined in claim 6 wherein the heterocyclic group is pyrryl, furyl, thienyl, pyridyl, pyranyl, pyrazolyl, imidazolyl, pyrimidinyl, or morpholinyl.

8. The compound of the Formula (I) defined in claim 1 wherein R is

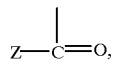

and Z is C1 to C4 alkyl or 14-eburnameninyl or is phenyl unsubstituted or substituted by halogen, C1 to C4 alkyl, C1 to C4 alkoxy, hydroxy, nitro, amino, cyano or trifluoromethyl, or a pharmaceutically acceptable salt thereof.

9. The compound of the Formula (I) defined in claim 8 selected from the group consisting of:

(a) (−)-trans apovincaminic acid 2-acetoxyethyl ester(3β, 16α);

(b) (−)-trans apovincaminic acid 2-(4-nitrobenzoyloxy) ethyl ester(3β, 16α);

(c) (−)-trans apovincaminic acid 2-(benzoyloxy)ethyl ester(3β, 16α);

(d) (−)-trans apovincaminic acid 2-(4-chlorobenzoyloxy) ethyl ester(3β, 16α);

(e) (−)-trans apovincaminic acid 2-propionyloxyethyl ester(3β, 16α);

(f) (−)-trans apovincaminic acid 2-(3,4,5-trimethoxybenzoyloxy)-ethyl ester(3β, 16α);

(g) (−) bis-trans apovincaminic acid ethyleneglycol ester (3β, 16α);

(h) (−)-trans apovincaminic acid 2-(benzoyloxy)ethyl ester(3α, 16β);

(i) (−)-trans apovincaminic acid 2-(4-chlorobenzoyloxy) ethyl ester (3α, 16β);

(j) (−)-trans apovincaminic acid 2-propionyloxyethyl ester(3α, 16β);

(k) (−)-trans apovincaminic acid 2-(3,4,5-trimethoxybenzoyloxy)-ethyl ester (3α, 16β);

(l) racemic trans apovincaminic acid 2-(acetoxy)ethyl ester; and (m) (−)-trans apovincaminic acid 3-(acetoxy)propyl ester (3β, 16α); or a pharmaceutically acceptable salt thereof.

10. A pharmaceutical composition for inhibiting lipid peroxidation and for treating ischemia which comprises a therapeutically effective amount of a compound of the Formula (I) as defined in claim 8 or a pharmaceutically acceptable salt thereof in combination with a pharmaceutically acceptable inert carrier.

11. A method of inhibiting lipid peroxidation, and of treating ischemia, which comprises the step of administering to a mammalian subject in need of said treatment, a therapeutically effective amount of the compound of the Formula (I) as defined in claim 8 or a pharmaceutically acceptable salt thereof alone or in combination with a pharmaceutically acceptable inert carrier.

* * * * *